United States Patent [19]

Perumattam

[11] Patent Number: 5,472,973
[45] Date of Patent: Dec. 5, 1995

[54] FLUORENYL DERIVATIVES AS ANTI-INFLAMMATORY AGENTS

[75] Inventor: John J. Perumattam, Baltimore, Md.

[73] Assignee: Scios Nova Inc., Mountain View, Calif.

[21] Appl. No.: 985,926

[22] Filed: Dec. 4, 1992

Related U.S. Application Data

[63] Continuation-in-part of Ser. No. 805,639, Dec. 12, 1991, abandoned.

[51] Int. Cl.$^6$ ............... C07D 257/04; C07C 333/08; C07C 229/42; A61K 31/245; A61K 31/41
[52] U.S. Cl. ............... 514/381; 514/480; 514/567; 558/240; 562/433; 548/251; 548/253
[58] Field of Search ............... 548/251, 253; 514/389, 480, 567; 562/433

[56] References Cited

U.S. PATENT DOCUMENTS

| | | | |
|---|---|---|---|
| 2,877,269 | 3/1959 | Campen et al. | 260/564 |
| 3,801,633 | 4/1974 | Toyoshima et al. | 260/518 |
| 3,835,175 | 9/1974 | Carpino et al. | 260/463 |
| 3,845,097 | 10/1974 | Toyoshima et al. | 260/471 |
| 3,906,031 | 9/1975 | Carpino et al. | 260/471 |
| 3,919,291 | 11/1975 | Toyoshima et al. | 260/482 |
| 5,079,260 | 1/1992 | Weitzberg et al. | 514/532 |

OTHER PUBLICATIONS

Rosenthale et al., "Immunopharmacologic Effects of Cycloleucine," In *Journal of Pharmacology and Experimental Therapeutics*, vol. 180, No. 2, pp. 501–513.

Ludwig et al., "MER–27, a Suppressant of Non–Bacterial Pneumonia in Mice," in *Proc. Soc. Exp. Biol. Med.*, vol. 100, pp. 495–497 (1959).

Carpino, "The 9–Fluorenylmethyloxycarbonyl Family of Base–Sensitive Amino–Protecting Groups," in *Accounts of Chemical Research*, vol. 20, pp. 401–407 (1987).

Burch et al., in "N–(Fluorenyl–9–methoxycarbonyl) amino acids, a class of anti–inflammatory agents with a different mechanism of action," *Proc. Natl. Acad. Sci. USA*, vol. 88, pp. 355–359, Jan. 1991.

*Primary Examiner*—David B. Springer
*Attorney, Agent, or Firm*—Nath & Associates; Gary M. Nath; Suet M. Chong

[57] ABSTRACT

The compound having the formula:

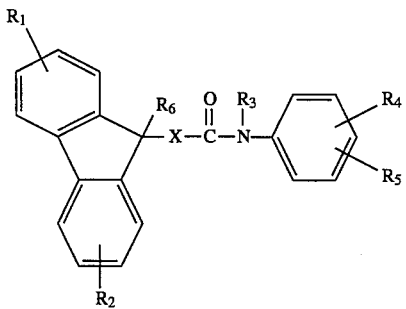

and a method of treating an inflammatory condition comprising administering to an animal in need of such treatment an effective amount of at least one compound represented by the formula.

28 Claims, No Drawings

FLUORENYL DERIVATIVES AS ANTI-INFLAMMATORY AGENTS

RELATED APPLICATIONS

This application is a Continuation-In-Part application of U.S. application Ser. No. 07/805,639 filed Dec. 12, 1991, now abandoned the entire contents of which are hereby incorporated by reference.

BACKGROUND OF THE INVENTION

1. Field of the Invention

This invention relates to novel fluorenyl derivative compounds, and more particularity to novel fluorenyl derivatives and pharmaceutical compositions suitable as anti-inflammatory agents.

2. Description of the Prior Art

The treatment of inflammatory conditions, such as atopic dermatitis, contact dermatitis, psoriasis, rheumatoid arthritis, glomerulonephritis, osteoarthritis, lupus erythematosus, scleroderma, asthma and irritable bowel disease has in the past, involved the use of agents such as aspirin-like nonsteroidal anti-inflammatory agents, glucocorticoids, methotrexate and cyclophosphamide. Unfortunately these agents generally produce unwanted side effects.

Nonsteroidal anti-inflammatory drugs (NSAIDs), while reducing inflammatory symptoms, do not prevent progression of disease and have serious side effects, including gastric ulceration. Glucocorticosteroids provide dramatic relief in some diseases but with systemic side effects, which often preclude chronic use at efficacious doses. Furthermore, certain cytotoxic agents can provide substantial relief but elicit major toxicity.

In contrast, methotrexate has been associated with patient death, cyclophosphamide has carcinogenic liability. Thus, new agents for treating inflammatory conditions that are free of these adverse side effects are needed.

Burch et al. in "N-(Fluorenyl-9-methoxycarbonyl) amino acids, a class of anti-inflammatory agents with a different mechanism of action", *Proc. Natl. Acad. Sci.* USA Vol 88, pp. 355–359, January 1991 discloses several members of a series of (N-fluorenyl-9-methoxycarbonyl) amino acids as possessing a broad spectrum of anti-inflammatory activity. The compounds are disclosed as being active against oxazolone dermatitis in mice and adjuvant arthritis in rat models in which activated T-lymphocytes are implicated. Burch et al. found that the compounds also inhibited T-lymphocyte activation in vitro, assessed by using the mixed lymphocyte reaction and that the compounds inhibited the reversed passive Arthus reaction in rats and arachidonic acid-induced dermatitis in mice models in which leukocyte infiltration is responsible for the inflammatory reaction.

SUMMARY OF THE INVENTION

The present invention relates to the formation of new fluorenyl compounds and more particularly to fluorenyl derivatives of various aminobenzoic acids. Applicants have unexpectedly discovered that the present compounds function as anti-inflammatory agents which do not act by inhibiting lipid metabolic enzymes. These materials are not steroids nor do they appear to increase the circulating levels of endogenous glucocorticoids. They do, however, appear to block recruitment of neutrophils into inflammatory lesions and may even inhibit T-cell activation.

In a preferred aspect of the invention the compounds of the invention have the formula:

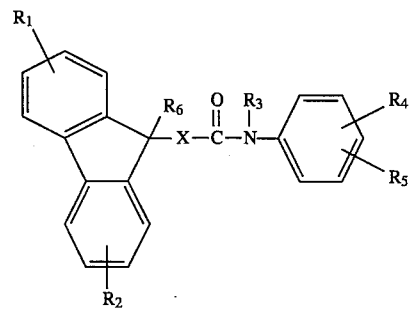

wherein

X is selected from the group consisting of methylene, oxygen, ethylene, methyleneoxy, and ethyleneoxy;

$R_1$ and $R_2$ are independently selected from the group consisting of hydrogen, $C_1$ to $C_6$ lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ lower alkyl groups;

$R_4$ is selected from the group consisting of -$CO_2H$, -$NHSO_2R_7$, wherein $R_7$ is methyl, or trifluoromethyl; -$CONHSO_2R_8$, wherein $R_8$ is methyl, trifluoromethyl, or phenyl; 1H-tetrazolyl-5-yl, -$(CH_2)_n$ COOH wherein n is 1, 2 or 3, and -$CO_2R_9$, wherein $R_9$ is hydrogen, $C_1$ to $C_6$ lower alkyl, aryl or 1-H-tetrazolyl-5-yl;

$R_5$ is selected from the group consisting of hydrogen, $C_1$ to $C_6$ lower alkyl, halogen, hydroxyl, and methoxy group; and $R_6$ is selected from the group consisting of hydrogen, halogen, $C_1$ to $C_6$ lower alkyl, $C_1$ to $C_6$ lower alkoxy, $C_1$ to $C_6$ lower alkoxy ethers, and alicyclic with hydrocarbo groups thereof.

Another aspect of the invention includes a method of treating an inflammatory condition comprising administering to an animal in need of such treatment an amount of at least one compound represented by the formula:

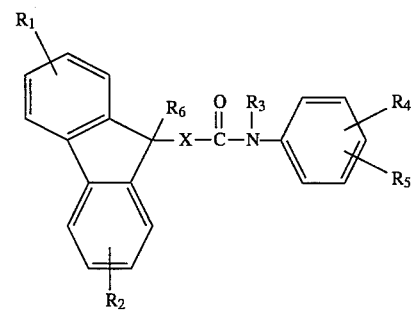

wherein:

X is selected from the group consisting of methylene, oxygen, ethylene, methyleneoxy, and ethyleneoxy;

$R_1$ and $R_2$ are independently selected from the group consisting of hydrogen, $C_1$ to $C_6$ lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ lower alkyl groups.

$R_4$ is selected from the group consisting of -$CO_2H$, -$NHSO_2R_9$, wherein $R_9$ is methyl, or trifluoromethyl;

-CONHSO$_2$R$_8$, wherein R$_8$ is methyl, trifluoromethyl, or phenyl; 1H-tetrazolyl-5-yl,-(CH$_2$)$_n$ COOH wherein n is 1, 2 or 3, and -CO$_2$R$_7$, wherein R$_7$ is hydrogen, C$_1$ to C$_6$ lower alkyl, aryl or 1-H-tetrazolyl-5-yl;

R$_5$ is selected from the group consisting of hydrogen, C$_1$ to C$_6$ lower alkyl, halogen, hydroxyl, and a methoxy group; and R$_6$ is selected from the group consisting of hydrogen, halogen, C$_1$ to C$_6$ lower alkyl, C$_1$ to C$_6$ lower alkoxy, C$_1$ to C$_6$ lower alkoxy ethers, and alicyclic with hydrocarbo groups thereof, or pharmaceutically acceptable salt thereof, sufficient to reduce or eliminate said inflammatory condition.

In another aspect of the invention the novel compounds are prepared as pharmaceutical compositions useful as anti-inflammatory agents. Such agents may be administered in many ways, such as topically, rectally, parenterally and orally.

DESCRIPTION OF THE PREFERRED EMBODIMENTS

The novel compounds of the invention have the formula:

wherein

X is selected from the group consisting of methylene, oxygen, ethylene, methyleneoxy. and ethyleneoxy;

R$_1$ and R$_2$ are independently selected from the group consisting of hydrogen, C$_1$ to C$_6$ lower alkyl, aryl, alkaryl, aralkyl, alkoxy, alkoxyalkyl, halogen, nitro and mixtures thereof;

R$_3$ is selected from the group consisting of hydrogen and C$_1$ to C$_6$ lower alkyl groups;

R$_4$ is selected from the group consisting of -CO$_2$H, -NHSO$_2$R$_7$, wherein R$_7$ is methyl, or trifluoromethyl; -CONHSO$_2$R$_8$, wherein R$_8$ is methyl, trifluoromethyl, or phenyl; 1H-tetrazolyl-5-yl,-(CH$_2$)$_n$ COOH wherein n is 1, 2 or 3, and -CO$_2$R$_9$, wherein R$_9$ is hydrogen, C$_1$ to C$_6$ lower alkyl, aryl or 1-H-tetrazolyl-5-yl;

R$_5$ is selected from the group consisting of hydrogen. C$_1$ to C$_6$ lower alkyl, halogen, hydroxyl, and a methoxy group; and R$_6$ is selected from the group consisting of hydrogen, halogen, C$_1$ to C$_6$ lower alkyl, C$_1$ to C$_6$ lower alkoxy, C$_1$ to C$_6$ lower alkoxy ethers, and alicyclic hydrocarbo groups thereof.

In a preferred feature of the invention, R$_1$, R$_2$ and R$_3$ are independently selected from the group consisting of hydrogen, chlorine and mixtures thereof. Alternatively, R$_1$ and R$_2$ are selected from the group consisting of 2,7-dimethyl, 2-7-diethyl, 2,7-di-t-butyl, and 2,7-dicyloro. Preferably, R$_4$ is selected from the group consisting of -2-CO$_2$H, -3-CO$_2$H, -4-CO$_2$H, and -4-CH$_2$CO$_2$H and R$_3$ is preferably selected from the group consisting of hydrogen, a hydroxyl group, and methyl group.

Exemplary compounds of the invention may be selected from the group consisting of:

N-[9H-(fluorenyl-9-ethoxycarbonyl)]amino-4-benzoic acid,

N-[9H-(2,7-dimethylfluorenyl-9-ethoxycarbonyl)] amino-4-benzoic acid,

N-[9H-(2,7-dichlorofluorenyl-9-ethoxycarbonyl)] amino-4-benzoic acid,

N-[9H-(2,7-di-t-butylfluorenyl-9-ethoxycarbonyl)]amino-4-benzoic acid,

N-[9H-(2,7-diethylfluorenyl-9-ethoxycarbonyl)]amino-4-benzoic acid,

N-[9H-(fluorenyl-9-ethoxycarbonyl)] -aminophenyltetrazole,

N-9H-(fluorenyl-9-ethoxycarbonyl)]amino-3-benzoic acid,

N-9H-(fluorenyl-9-ethoxycarbonyl)]anthranilic acid,

N-[3-(9-fluorenyl)propionyl] anthranilic acid,

N-[9H-(fluorenyl-9-methoxycarbonyl)]-N-methylanthranilic acid,

N-[9H-(fluorenyl-9-ethoxycarbonyl)]-4-aminosalicylic acid,

N-[3-(9-fluorenyl)propionyl]-4-aminosalicylic acid,

N-[9H-(fluorenyl-9-methoxycarbonyl)]-4-aminophenyl acetic acid,

N-[9H-(fluorenyl-9-ethoxycarbonyl)]-4-aminophenylacetic acid,

N-9H-(fluorenyl-9-methoxycarbonyl)]-4-aminophenyl-α-methylacetic acid,

N-(fluorenyl-9-methoxycarbonyl)-N$^1$-acetylsulfanilamide,

N-{2-[9-methyl-9H-fluoren-9-yl]-ethoxycarbonyl-4-aminobenzoic acid,

N-{2-[9-ethyl-9H-fluoren-9-yl]-ethoxycarbonyl-4-aminobenzoic acid,

N-[9-methyl-(2,7-dichlorofluorenyl-9-ethoxycarbonyl)]-4-aminobenzoic acid,

N-[9-ethyl-(2,7-dichlorofluorenyl-9-ethoxycarbonyl)]-4-aminobenzoic acid, 9-methyl-N-[3-(9-(2,7-dichlorofluorenyl)propionyl]-4-aminobenzoic acid, 9-methyl-N-[3-(9-fluorenyl))propionyl]-4-aminobenzoic acid, N-(9H-fluorenyl-9-oxycarbonyl)-4-aminobenzoic acid, and N-{[9H-(fluorenyl-9-ethoxycarbonyl)]-4-amino-benzoyl}-benzenesulfonamide.

Of the exemplified compounds, particularly preferred compounds which exhibit activity even when taken orally are N-[9H-(fluorenyl-9-ethoxycarbonyl)]amino-4-benzoic acid, N-[ 9H-(2,7-dimethylfluorenyl-9-ethoxycarbonyl)]-amino-4-benzoic acid, N-[9H-(2,7-dichlorofluorenyl-9-ethoxycarbonyl)] -amino-4-benzoic acid, N-(9H-fluorenyl-9-oxycarbonyl)- 4-aminobenzoic acid, and N-{[9H-(fluorenyl-9-ethoxycarbonyl)] -4-amino-benzoyl}-benzenesulfonamide.

The terms used herein are used in their conventional manner, for example, "halogen" includes bromo, fluoro, chloro and iodo; "aryl" is an aromatic ring compound such as benzene, phenyl, naphthyl and substituted forms thereof; "aralkyl" is an aryl being attached through an alkyl chain, straight or branched, of from one through six carbons, and so forth;" "alicyclic" is an organic compound characterized by a closed ring structure and include cycloparaffins, cycloolefins and cycloacetylenes.

The present inventive subject matter also entails a method of treating an inflammatory condition comprising administering to an animal in need of such treatment an amount of at least one compound represented by the following formula:

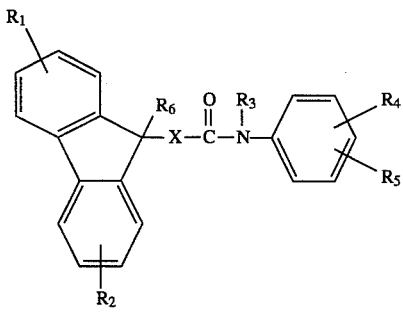

wherein

X is selected from the group consisting of methylene, oxygen, ethylene, methyleneoxy, and ethyleneoxy;

$R_1$ and $R_2$ are independently selected from the group consisting of hydrogen, $C_1$ to $C_6$ lower alkyl, aryl, alkaryl, aralkyl, alkoxy, alkoxyalkyl, halogen, nitro and mixtures thereof;

$R_3$ is selected from the group consisting of hydrogen and $C_1$ to $C_6$ lower alkyl groups.

$R_4$ is selected from the group consisting of -$CO_2H$, -$NHSO_2R_7$, wherein $R_7$ is methyl, or trifluoromethyl; -$CONHSO_2R_8$, wherein $R_8$ is methyl, trifluoromethyl, or phenyl; 1H-tetrazolyl-5-yl,-$(CH_2)_n$ COOH wherein n is 1, 2 or 3, and -$CO_2R_9$, wherein $R_9$ is hydrogen, $C_1$ to $C_6$ lower alkyl, aryl or 1-H-tetrazolyl-5-yl;

$R_5$ is selected from the group consisting of hydrogen, $C_1$ to $C_6$ lower alkyl, halogen, hydroxyl, and a methoxy group; and $R_6$ is selected from the group consisting of hydrogen, halogen, $C_1$ to $C_6$ lower alkyl, $C_1$ to $C_6$ lower alkoxy, $C_1$ to $C_6$ lower alkoxy ethers, and alicyclic with hydrocarbo groups thereof, as well as pharmaceutical compositions containing the same.

The preparation of compounds for administration in pharmaceutical preparations may be accomplished in a variety of well known methods known to those skilled in the art of synthetic organic chemistry. Appropriate pharmaceutically acceptable salts within the scope of the invention are those derived from mineral acids such as hydrochloric acid, phosphoric acid, nitric acid and sulfuric acid; and organic acids such as tartaric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skill in the art. Merely for purposes of illustration, the class may be said to include mono-, di- and trialkylamines, such as methylamine, dimethylamine, and triethylamine; mono-, di- or trihydroxyalkylamines such as mono-, di-, and triethanolamine; amino acids such as arginine, lysine; guanidine; N-methyl-glucosamine; n-methylglucamine; L-glutamine-N-methylpiperazine; morphonline; ethylenediamine; N-benzylphenethylamine; tris(hydroxymethyl)aminomethane; and the like. (See for example, "Pharmaceutical Salts," J . Pharm. Sci. (1977) 66 (1): 1–19.)

The compounds can be incorporated into convenient pharmaceutical dosage forms such as capsules, tablets, or injectable preparations. Solid or liquid pharmaceutical carriers can be employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, along or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques well known to a pharmaceutical chemist involving mixing, granulating, and compressing when necessary, for tablet forms, or mixing, filling, and dissolving the ingredients, as appropriate, to give the desired oral or parenteral products.

In parenteral administration (i.p.) of the novel compounds and compositions of the invention, they may be formulated in aqueous injection solutions which may contain antioxidants, buffers, bacteriostats, and so forth. Extemporaneous injection solutions may be prepared form sterile pills, granules or tablets which may contain diluents, dispersing and surface active agents, binders and lubricants.

In the case of oral administration, fine powders or granules of the compound may be formulated with diluents as well as dispersing and surface active agents. They may also be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the pharmaceutical art.

Preferably, the pharmaceutical compositions of the invention include the active ingredient in a quantity selected from 5 mg to 1000 mg, advantageously, from about 10 mg to 500 mg, per dosage unit, depending on the route of administration. Appropriate concentrations and dosage unit sizes can be readily determined by one of ordinary skill in the art.

As indicated above, the pharmaceutical compositions of the invention can be present in dosage unit form. For example, the composition can take the form of a tablet (preferably enteric coated), capsule, powder, troche, lozenge, inhalant, syrup, emulsion, gel, ointment, cream, lotion, transdermal patch, suppository, sterile injectable liquid as well as a liquid suspension or solution.

The method of treating an inflammatory condition according to this invention comprises administering to a subject in need of such treatment an effective amount of at least one of the novel compounds sufficient to produce an anti-inflammatory effect. The inventive compounds can be administered orally, nasally, topically, transdermally, parenterally or rectally, as may be required to effect the desired anti-inflammatory effect.

The active ingredient will normally be administered in a daily dosage regimen selected from about 10 mg to 1 g, most preferably from about 20 mg to about 500 mg. Advantageously, between one time per day to one time per week. The frequency of administration and the amount of active ingredient to be administered to effect treatment of a particular inflammatory condition can readily be determined by one skilled in the art. For inflammatory conditions of the lungs, an aerosol dispensing system wherein the active medicament is incorporated with an inert propellant in an aerosol container is of particular applicability. Such an aerosol system will deliver a metered dose of about 100 mcg to about 650 mcg, administered once or twice at a time as needed.

The novel compounds described herein may be prepared by methods well known in the art and as exemplified below. For example, details of general synthetic procedures involve the following reactions.

General Methods of Preparation of the Claimed Compounds

The compounds of Examples 1 to 6 were prepared according to the scheme as outlined below (Scheme 1). The fluorene-9-methanol was converted into the corresponding chloroformate using phosgene and is then coupled with p-aminobenzoic acid.

Scheme 1

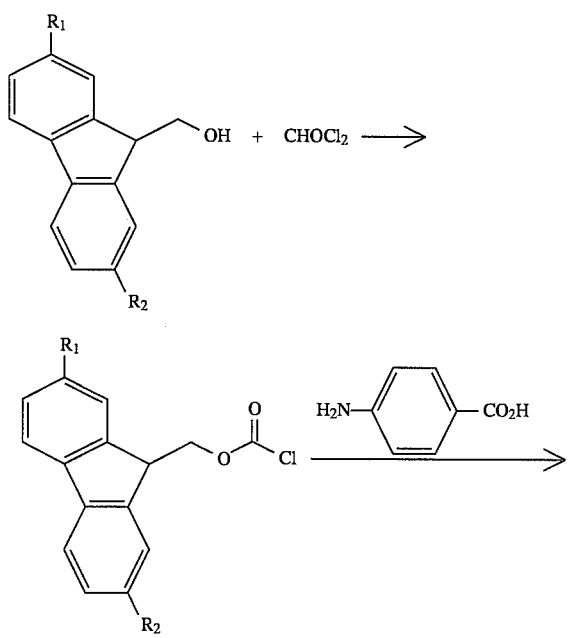

-continued
Scheme 1

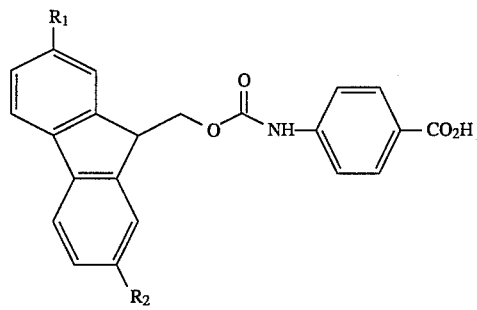

Compounds in Examples 7 to 13 were prepared by the general scheme as shown below (Scheme 2). The fluorene anion was treated with ethylene oxide to generate fluorene-9-ethanol which is converted to chloroformate using phosgene, then coupled with aminobenzoic acids.

Scheme 2

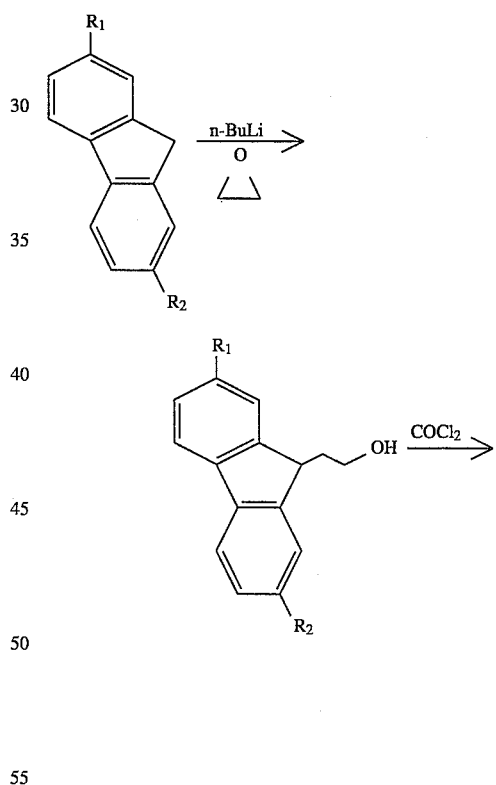

-continued
Scheme 2

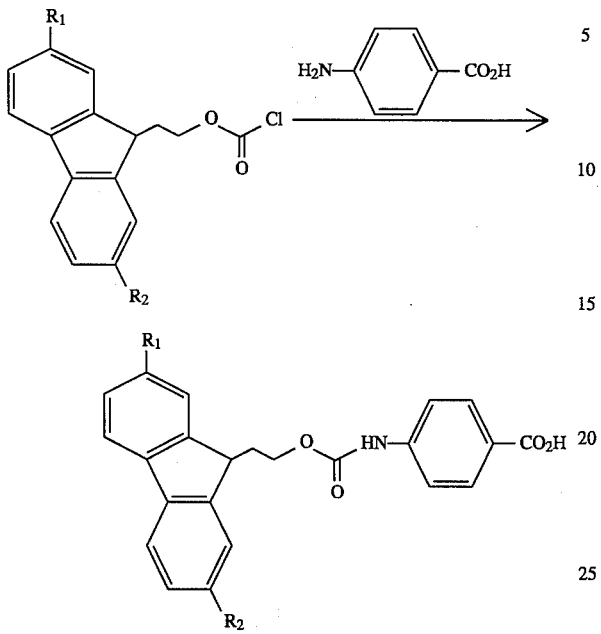

The compounds in Examples 14 and 15 were prepared according to the general scheme (Scheme 3) as shown below. The fluorene anion is quenched with 2-(2-bromoethyl)-1,3-dioxalane and the product was oxidized using Jone's reagent to provide the acid. Thionyl chloride treatment of the acid gave the acid chloride which was then coupled with aminobenzoic acids.

Scheme 3

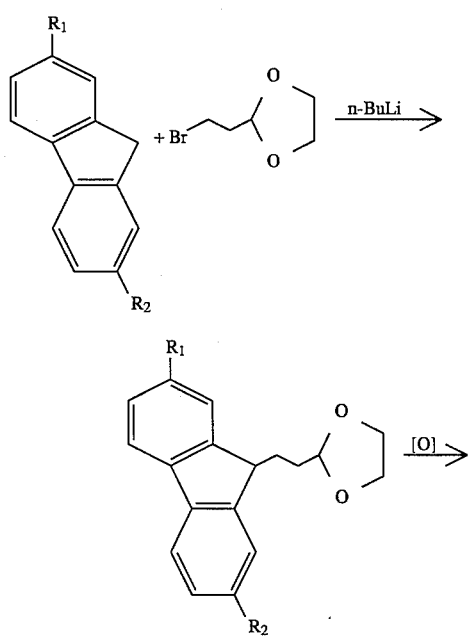

-continued
Scheme 3

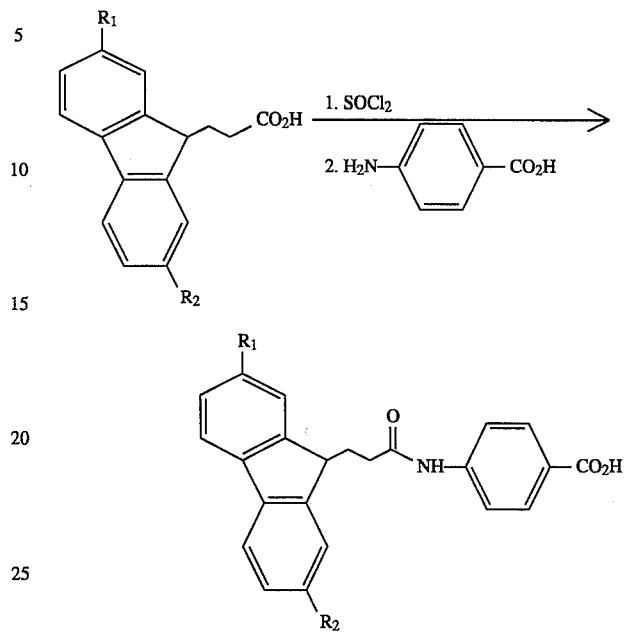

The activity of the present compounds as anti-inflammatory agents can be demonstrated in animals, such as mice, for example, by measuring the ability of the compound to inhibit edema caused by a variety of inflammatory agents that are generally accepted as producing irritation by differing mechanisms. Such inflammatory agents typically include oxazolone, and the like. The reverse passive Arthus test offers another measure of the compound's utility in preventing an inflammatory response (Chang et al. Eur. J. Phar. 69:155–164 (1981)). Test compounds are typically administered intraperitoneally or orally. For intraperitoneal administration, the test compound can be given in dimethyl sulfoxide or in 0.5% methylcellulose 30 minutes prior to administration of the irritant. For oral administration, the test compound can be compounded into tablet or capsule form as well as dissolved in, for example, water or ethanol and swallowed prior to application of the irritant. Results can be expressed as the percent decrease in swelling in the compound-treated animals as compared to control animals that receive only the irritant.

It is noteworthy that currently available non-steroidal anti-inflammatory agents operate by a single mechanism (cyclo-oxygenase inhibitors), thus, they are highly active in a single assay (steroids are usually active in most, if not all, screens but have side effects that prohibit their widespread use). The compounds are highly active in almost all of the inflammatory screens and are also highly active in the reverse passive Arthus assay and in adjuvant arthritis, which are considered to be predictive of activity against human arthritis. That is, the present compounds have the steroid-like spectrum of activity but lack steroid-like toxicity.

The following non-limiting Examples, which are illustrative of the compounds suitable for use in the methods and compositions of the present invention, demonstrate the activity of these compounds as well as processes for their preparation.

Examples 1 to 6 demonstrates the formation of compounds having the general structure:

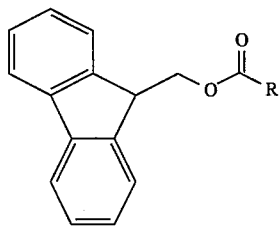

EXAMPLE 1

N-[9-H-(Fluorenyl-9-methoxycarbonyl)]anthranilic acid

To a clear solution containing 500 mg (3.26 mmol) of anthranilic acid and 450 mg (3.26 mmol) of potassium carbonate in 10 ml of water was added 765 mg (2.96 mmol) of fluorenylmethoxycarbonyl chloride in 10 ml of dioxane. The mixture was stirred at room temperature (22° C.) for 2.5 hours. Evaporation of the solvent gave an oil which was dissolved in water and acidified with 10% HCl whereupon a white solid separated. This was collected by filtration and dried. Recrystallization from 10% ethyl and acetate/hexane mixture provides a white solid (450 mg, 45%, mp 212°–214°. IR (KBr) 1738, 1668, 1591, 1527, 1450, 1262, 1213, 1054, 758 CM$^{-1}$; $^1$H NMR (DMSO, 300 MHZ) 4.28 (t, 1H, J=8.2 Hz), 4.39 (d, 2H, J=7.2 Hz), 7.02 (t, 1H, J=7.6 Hz), 7.63 (d, 1H, J=7.6 Hz), 7.82(d, 2H, J=7.6 Hz) 7.95(d, 1H, J=7.6 Hz), 8.17(t, 1H, J=7.6 Hz), 11.17 (br, 1H), anal. calcd for $C_{22}H_{17}NO_4$: C, 73.53; H, 4.77; N, 3.90. Found C, 7.27; H, 4.82; N, 3.83.

EXAMPLE 2

N-[9H-Fluoren-9-ylmethoxy)carbonyl]-4-aminosalicylic acid

To a solution containing 1.0 g(6.5 mmol) of 4-aminosalicylic acid, 898 mg(6.5 mmol) of $K_2CO_3$ in 15 ml of dioxane and 5 ml of water was added 9-fluorenylmethyl chloroformate in 5 ml of dioxane. The reaction mixture was stirred for 2 hours at room temperature (22° C.) and the dioxane evaporated. The residue was diluted with water and extracted with ethyl acetate. The basic aqueous solution was then acidified with 10% HCl, the separated solids were collected by filtration and dried (1.85 g, 75%), mp 234°–235° C. (subl.). IR (KBr) 3342, 3016, 1715, 1643, 1594, 1519, 1450, 1229, 1198, 1110, 1056 cm$^{-1}$. NMR (300 MHz, DMSO-$d_6$)∂ 4.21 (t, 1H, J=6.6 Hz), 4.41 (d, 2H, J=6.6 Hz), 6.81–7.82 (m, 12H), 9.7 (s, 1H). Anal. Calcd for $C_{22}H_{17}NO_5$: C, 70.39; H, 4.56; N, 3.73. Found: C, 70.24; H, 4.59; N, 3.67.

EXAMPLE 3

N-[9H-(Fluorenyl-9-methoxycarbonyl)]-4-aminophenylacetic acid

To a solution of 9-fluorenyl methylchloroformate (2.0 g, 8 mmol) to 10 ml of dioxane was added dropwise with stirring a solution of 4-aminophenylacetic acid (1.28 g, 8.4 mmol) and potassium carbonate (1.16 g, 8.4 mmol) in 10 ml of water. A brown precipitate formed, and the solution was stirred for 2 hours, diluted with water, and acidified with 10% HCl. Concentration yielded a brown solid which was recrystallized two times for methanol, washed with hexane and dried to give white crystals of N-[9H-(Fluorenyl-9-methoxycarbonyl)]-4-aminophenylacetic acid (1.9 g 34% yield) mp 169° C. FTIR(KBr) 3319, 1702, 1599, 1529, 1450, 1419, 1316, 1244, 1229, 1108, 1092, 1051, 740 cm$^{-1}$. $^1$H NMR(300 MHz, DMSO) δ 3.45 (S, 2H), 4.28 (t, 1H, J=6.5 Hz), 4.44 (d, 2H, J=6.5 Hz), 7.12 (d, 2H, J=7.5 Hz), 7.35 (m, 7H), 7.72 (d, 2H, J=7.5 Hz), 7.88 (d, 2H, J=7.5 Hz), 9.64 (s, 1H). Anal. calcd for $C_{22}H_{19}NO_4 \cdot 0.5H_2O$: C, 72.24; h, 5.27; N, 3.66. Found: C, 72.41; H, 5.26; H, 3.91.

EXAMPLE 4

N-[9H-(Fluorenyl-9-methoxycarbonyl)]-N-mmethylanthranilic acid

To a solution of 9-fluorenylmethyl chloroformate (1.0 g, 3.9 mmol) in 10 ml of dioxane, was added dropwise with stirring a solution of N-methylanthranilic acid (0.60 g, 4.0 mmol) and potassium carbonate (0.55 g, 4.0 mmol) in 10 ml of water and 2 ml of dioxane. After 1 hour the solution was concentrated, suspended in 100 ml of water, and decanted from an oil. Acidification with 10% HCl yielded a tan solid of N-[9H-(Fluorenyl-9-methmoxycarbonyl)]-N-methylanthranilic acid, which was filtered off, washed with water, then hexane, and dried (0.6 g, 38%). mp 69°–72° C. FTIR(KBr) 3052, 1712, 1601, 1447, 1401, 1437, 1306, 1167, 1072, 1000, 768, 740, 712 cm$^{-1}$. $^1$H NMR (300 MHz, CDCl$_3$) δ 3.28 (m, 1H, 4.02 (m, 1H), 4.32 (m, 2H), 7.09–8.11 (m, 12H). Anal. calcd for $C_{23}H_{19}NO_4 \cdot 0.75 H_2O$): C, 71.39; H, 5.34; N, 3.62. Found: C,71.23; H, 5.18; N, 3.64.

EXAMPLE 5

N-[9H-(Fluorenyl-9-methoxycarbonyl)]-4-aminophenyl-α-methylacetic acid

To a solution of 9-fluorenylmethyl chloroformate (1.68 g, 6.5 mmol) in 15 ml of dioxane was added dropwise with stirring a solution of 4-aminophenyl-α-methylacetic acid (1.0 g, 6.1 mmol) and potassium carbonate (2.07 g, 15 mmol) in 10 ml of water and 5 ml of dioxane. After 0.5 hours the solution was concentrated to remove the dioxane, suspended in 75 ml of water, and acidified with 10% HCl to yield a white precipitate which coagulated. The precipitate was removed, dried, broken into pieces, and washed with water, then hexane, and dried again. The solid was slurried in hot ethyl acetate, and filtered to give a white solid, 0.82 g (34%), mp 157°–160° C. FTIR 3334, 1704, 1596, 1529, 1452, 1419, 1308, 1234, 1095, 1409, 761, 748 cm$^{-1}$. $^1$HNMR (300 MHz, DMSO) δ 9.60 (s, 1H), 7.88 (d, 2H, J=7.0 Hz), 7.43 (d, 2H, J=7.0 Hz), 7.27–7.43 (m, 6H), 7.13 (d, 2H, J=8.0 Hz), 4.93 (d, 2H, J=6.5 Hz), 4.27 (t, 1H, J=6.5 Hz), 3.42 (m, 1H), 1.24 (d, 3H, J=7.0 Hz). Anal. calcd for $C_{24}H_{21}NO_4 \cdot 1.25 H_2O$: C, 70.31: H, 5.7: N, 3.41. Found: C, 70.66; H, 5.52:, N, 3.44.

EXAMPLE 6

N-(Fluorenyl-9-methoxycarbonyl)-N$^1$-acetylsulfanilamide

To a solution of 9-fluorenylmethyl chloroformate (1.0 g, 3.9 mmol) in 10 ml of dioxane was added dropwise with stirring a solution of N-acetylsulfanilamide sodium salt hydrate (0.92 g, 4.0 mmol) and potassium carbonate (0.62 g, 4.5 mmol) in 10 ml of water. After 2 hours the solution was concentrated, suspended in water, and acidified to pH 3 with 10% HCl to yield a white precipitate which was filtered off and dried to give 1.38 g (83%), mp 223°–227° C. FTIR (KBr) 3270, 1715, 1594, 1529, 1447, 1409, 1321, 1159, 1090, 1046 1002, 941, 869, 833, 740 cm$^{-1}$. $^{1}$HNMR (330 MHz, DMSO) δ 1.88 (s, 1H), 4.31 (t, 1H, J=7.5 Hz), 4.53 (d, 2H, J=6.5 Hz), 7.28–7.91 (m, 12H), 10.19 (s, 1H), 11.94 (s, 1H). Anal. calcd for $C_{23}H_{20}N_{2}O_{5}S$: C, 63.29; H, 4.62;, n, 6.42. Found: C, 63.42; H, 4.63; N, 6.33.

Examples 7 to 13 demonstrate the formation of compounds having the general structure:

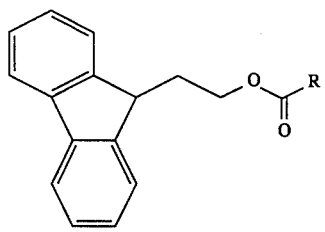

EXAMPLE 7

N-[9H-(Fluorenyl-9-ethoxycarbonyl)]amino-4-benzoic acid 2-(9-Fluorenyl)ethanol was prepared from a solution of fluorene (116.35 g, 0.7 mmol) in 800 ml of dry THF at −20° C. which was added n-BuLi in hexane (0.7 mol) keeping the temperature below −10° C. To the clear solution was rapidly added 357 ml of 1.4M ethylene oxide in ether (0.5 mol) keeping the temperature below 5° C. The reaction mixture was stirred for 5 hours, then quenched with 50 ml of saturated ammonium chloride solution. The THF was removed at a rotary evaporator. The residue was partitioned between water and ethyl acetate. The organic layer was separated, dried with $MgSO_{4}$ and concentrated in vacuo until crystallization began. The solution was allowed to stand overnight and the crystals were collected and dried (mp 97° C.) (85.5 g, (81%)).

N-[9H-(Fluorenyl-9-ethoxycarbonyl)]amino-4-benzoic acid was prepared from a solution of 2-(9-fluorenyl) ethanol (1.5 g, 7.1 mmol) in 10 ml of toluene to which was added dropwise with stirring a solution of phosgene in toluene (12.4 ml, 1.93M). After 0.5 hours, the solution was put under vacuum to remove excess phosgene, and concentrated to yield 2-(9-fluorenyl)ethyl chloroformate. This was then dissolved in 10 ml of dioxane and add to a solution of 4-aminobenzoic acid (1.0 g, 7.3 mmol) in 15 ml water. After 5 hours, the dioxane was evaporated, the solution diluted with an equal amount of water, rendered basic with sodium carbonate solution, and filtered to remove insoluble materials. Acidification with 10% HCl yielded a white precipitate, which was filtered and dried. Crystallization from aqueous DMF gave a white solid (1.22 g, 46%), mp 202° C. IR(KBr) 3342, 2964, 2666, 2543, 2363, 1699, 1676, 1609, 1594, 1524, 1509, 1477, 1414, 1313, 1293, 1266, 1177, 1069, 1049, 938, 853, 768, 750, 735 cm$^{-1}$. $^{1}$H NMR (300 MHz, DMSO) δ 2.3(q, 2H, J=7.0), 400(t, 2H, J=7.0), 4.12(t, 1H, J=6.0), 7.29–7.88(m, 13H, 9.97(s, 1H). Anal. calcd for $C_{23}H_{19}NO_{4}0.25H_{2}O$: C, 73.10; H, 5.20; N, 3.71. Found: C, 73.32; H, 5.23; H, 3.70.

EXAMPLE 8

N-[9H-(2,7-Dimethylfluorenyl-9-ethoxycarbonyl)]amino-4 -benzoic acid

This compound is prepared according to the procedure of Example 1 using 2-[9-(2,7-dimethylfluorenyl)] ethanol as the starting material instead of 2-(9-fluorenyl) ethanol.

EXAMPLE 9

N-[9H-(2,7-Dichlorofluorenyl-9-ethoxycarbonyl)amino-4 -benzoic acid

This compound is prepared according to Example 8 using 2-[9-(2,7-dichlorofluorenyl)] ethanol as the starting material.

EXAMPLE 10

N-[9H-(Fluorenyl-9-ethoxycarbonyl)amino-3-benzoic acid

This compound is prepared according to Example 1 using 3-aminobenzoic acid instead of 4-aminobenzoic acid.

EXAMPLE 11

N-[9H-(Fluorenyl-9-ethoxycarbonyl)anthranilic acid

A phosgene solution (12.4 ml of a 1.93M solution in toluene) was added dropwise with stirring to a solution of 2-(9-fluorenyl)ethanol (1.26 g, 6 mmol). After 0.5 hours the solution was put under vacuum to remove the phosgene, and concentrated to give 2-(9-fluorenyl)ethyl chlormoformate (1.64 g, 6 mmol). This was dissolved in 10 ml dioxane, and to it added dropwise a solution of anthranilic acid (0.85 g, 6.2 mmol) and potassium carbonate (0.86 g, 6.2 mmol) in 15 ml water. After 3 hours, the dioxane was evaporated, and the solution diluted with an equal amount of water. Acidification with 10% HCl yielded a white precipitate which was washed with water and dried. (1.98 g, 88%), mp 177° C. IR(KBr) 3175, 1709, 1684, 1594, 1537, 1450, 1380, 1301, 1259, 1205, 1146, 1049, 753,740 cm$^{-1}$. $^{1}$HNMR (300 MHz, CDCl$_{3}$) δ 2.46 (q, 2H, J=6.8), 4.14 (t, 3H, J=6.8), 7.10 (t, 1H, J=6.5), 8.46 (m, 13H), 10.13 (s, 1H). Anal. calcd for $C_{23}H_{19}NO_{4}$: C, 73.98; H, 5.13; N, 3.75. Found: C, 73.87; H, 5.19; N, 3.73.

EXAMPLE 12

N-[9H-(Fluorenyl-9-ethoxycarbonyl)]-4-aminosalicylic acid

To a solution of 2-(9-fluorenyl)ethanol 1.26 g, 6 mmol) in 10 ml of toluene and 4 ml of tetrahydrofuran (THF), was added dropwise with stirring phosgene (12.4 ml, 1.93M solution in toluene). The solution was stirred for 0.5 hours, then put under vacuum to remove the phosgene. Concentration yielded 2-(9-fluorenyl)ethyl chloroformate (6 mmol, 1.64 g).

To a solution of 4-aminosalicylic acid (0.95 g, 6.2 mmol) and potassium carbonate (0.82 g, 6.2 mmol) in 15 ml of water, was added dropwise with stirring a solution of 2-(9-fluorenyl)ethyl chloroformate (1.64 g, 6.0 mmol) in 10 ml of dioxane. The solution was concentrated after 2 hours, then diluted with water and made basic with 10% sodium carbonate. Acidification with 10% HCl yielded N-[ 9H-(Fluorenyl-9-ethoxy carbonyl)]-4-aminosalicylic acid, which was filtered off and purified by reverse phase chromatography (C$_{18}$) using methanol/water, 6:4 as eluent to give 0.66 g (28%) of a solid, mp 230° C. FTIR(KBr) 3396, 3013, 1753, 1655, 1617, 1517, 1478, 1442, 1288, 1275, 1262, 1211, 1175, 1105, 1051, 1010, 959, 851, 786, 753, 735 cm$^{-1}$. $^{1}$HNMR (300 MHz, DMSO) δ 2.30 (q, 2H, J=3.5 Hz), 4.00 (t, 2H, J=3.5 Hz), 4.12 (t, 1H, J=3.5 Hz), 6.91–7.8(m, 11H).

Anal. calcd for $C_{23}H_{19}N_5O$: C, 70.94; H, 4.92; N, 3.60. Found: C, 70.86; H, 4.97; N, 3.56.

EXAMPLE 13

N-[9H-(Fluorenyl-9-ethoxycarbonyl)]-4-aminophenylacetic acid 2-(9-Fluorenyl)ethyl chloroformate was prepared from a solution of 2-(9-fluorenyl)ethanol (1.26 g, 6.0 mmol) in 10 ml of toluene and 4 ml of tetrahydrofuran, which was added to 12 ml of phosgene solution (12.4 mol, [1.93M in toluene). The solution was stirred for 1 hour and put under vacuum to remove the phosgene. Concentration yielded 2-(9-fluorenyl-)ethyl chloroformate (1.64 g, 6.0 mmol).

N-[9H-(Fluorenyl-9-ethoxycarbonyl)]-4-aminophenylacetic acid was prepared from a solution of 4-aminophenylacetic acid (0.94 g, 6.2 mmol) and potassium carbonate (0.86 g, 6.2 mmol) in 10 ml of water, which was added dropwise with stirring to a solution of 2-(9-fluorenyl)ethyl chloroformate (1.64 g, 6.0 mmol) in 10 ml of dioxane. After 4 hours the solution was concentrated, diluted with water and acidified with 10% HCl. A precipitate formed, and was purified by reverse phase chromatography, eluting with methanol/water, 6:4 to give N-[9H- (Fluorenyl-9 -ethoxycarbonyl)-4-aminophenylacetic acid (0.90 g, 38%), mp 107° C. IR(KBr) 3314, 3041, 2980, 2933, 2365, 1697, 1604, 1532, 1447, 1475, 1414, 1239, 1077, 1056, 804, 758, 745, 673, 527 cm$^{-1}$. $^1$H NMR (300 MHz, DMSO): δ 9.55(s, 1H), 7.87(d, 2H, J=6.5 Hz), 7.62(d, 2H, J=6.5 Hz), 7.35(m, 6H), 7.10(d, 2H, J=8.3 Hz), 4.12(t, 1H, J=7.0 Hz), 3.98(t, 2H, J=7.0 Hz), 3.45(s, 1H), 2.28(q, 2H, J=7.0 Hz). Anal. calcd for $C_{24}H_{21}NO_4 0.25 H_2O$: C, 73.54; H, 5.53; H, 3.57. Found: C, 73.89; H, 5.53; n, 3.60

Examples 14 and 15 demonstrate the formation of compounds having the general structure:

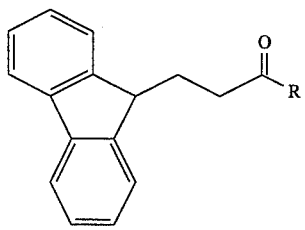

EXAMPLE 14

N-[3-(9-Fluorenyl)propionyl]anthranilic acid 2-(9-Fluorenyl)ethyl-1,3-dioxolane was prepared from a solution of fluorene (30.0 g, 180.5 mmol) in 400 ml of dry THF cooled in a −78° C. bath under argon, to which was added 100 ml of n-butyllithium (2.0M in cyclohexane) over 15 minutes. After stirring for 0.5 hours at 78° C., 2-( 2-bromoethyl)-1,3-dioxolane (22.3 ml, 190 mmol) was added dropwise, and the resulting solution stirred at room temperature for 16 hours. Concentration in vacuo yielded an orange residue which was partitioned between ethyl acetate and saturated ammonium chloride. The organic layer was then washed with brine, dried with magnesium sulfate, and concentrated in vacuo to afford an orange oil. Flash chromatography on silica, hexane:ethyl acetate 20:1 to 1:1 yielded a yellow oil (36.38 g, 76%).

3-(9-Fluorenyl)propionic acid was prepared from 2-(9-fluorenyl)ethyl-1,3-dioxolane (50.0 g, 187 mmol) which was dissolved in 20 ml of acetone and 450 ml of Jones' reagent (64 g chromic acid and 64 ml of sulfuric acid in 400 ml of water). After the reaction was complete, the acetone was evaporated, the residue taken into ethyl acetate, washed with water, and organic layer extracted with 1N sodium hydroxide which was acidified with 10% HCl to yield a tan precipitate. FTIR 1954, 1913, 1707, 1429, 1316, 1257, 1208, 948, 933, 735 cm$^{-1}$. $^1$H NMR (300 MHz, DMSO-di$_s$) δ 1.84 (t, 2H, J=7.5 Hz), 2.21 (m, 2H), 4.03 (t, 2H, J=5.5 Hz), 7.28–7.38 (m, 4H), 7.56 (d, 2H, J=7.0 Hz), 7.84 (d, 2H, J=7.0 Hz).

To prepare 3-(9-fluorenyl)propionic acid chloride, 3-(9-fluorenyl)propionic acid (1.0 g, 4.2 mmol) was refluxed in 5 ml of thionyl chloride for 1.5 hours. The solution was then concentrated to a brown oil, which solidified under high vacuum.

To prepare N-[3-(9-fluorenyl)propionyl]-anthranilic acid a solution of anthranilic acid (0.57 g, 4.2 mmol and 0.65 ml pyridine 8.4 mmol) in 15 ml of methylene chloride was added dropwise with stirring a solution of 3-(9-fluorenyl-)propionic acid chloride (1.10 g, 4.2 mmol) in 10 ml of methylene chloride. After 6 hours, the solution was then washed with 10% HCl, then brine, dried with magnesium sulfate, and concentrated to give 1.40 g (92%), of a white solid, mp 167°–172° C. FTIR (KBr) 3332, 1679, 1601, 1583, 1532, 1457, 1411, 1259, 1167 cm$^{-1}$. $^1$H NMR (300 MHz, DMSO) δ 2.02(t, 2H, J=7.0 Hz), 2.37 (m, 2H), 4.10 (t, 1H, J=6.5 Hz), 7.07–7.91 (m, 12H), 8.35 (d, 1H, J=8.0 Hz). Anal. calcd for $C_{23}H_{19}NO_3$: C, 77.29; H, 5.35; N, 3.92. Found: C, 77.16; H, 5.36; N, 3.84.

EXAMPLE 15

N-[3-(9-Fluorenyl)propionyl]-4-aminosalicylic acid

Preparation of N-[3-(9-Fluorenyl)propionyl]-4-aminosalicylic acid hydrate was performed as follows. 2-(9-Fluorenyl)propionic acid (1.0 g, 4.2 mmol) was refluxed in 5 ml of thionyl chloride for 1.5 hours and the excess thionyl chloride evaporated in vacuo. The residue was dissolved in 10 ml of methylene chloride and added dropwise to a suspension of 4-aminosalicylic acid (0.64, 4.2 mmol) and pyridine (0.65 ml 8.4 mmol) in 15 ml of methylene chloride. After 3 hours, the reaction was concentrated, taken into ethyl acetate, washed with 10% HCl, and the organic layer dried with magnesium sulfate and concentrated to a tan solid which was purified by reverse phase flash chromatography ($C_{18}$) eluting with methanol/water 50/50 then 70/30 to give a white solid, mp 225°–228° C. FTIR (KBr) 1643, 1511, 1450, 1367, 1257, 1167, 879, 830, 740, 671 cm$^{-1}$. $^1$H NMR (300 MHz, DMSO) δ 1.92 (t, 2H, J=7.5 Hz), 2.35 (m, 2H), 4.09 (t, 1H, J=5.0 Hz), 6.92 (dd, 1H, J=8.5 Hz), 7.24–7.39 (m, 8H), 7.61 (m, 2H), 7.86 (d, 2H, J=7.5 Hz) 9.94 (s, 1H). Anal. calcd for $C_{23}H_{19}NO_4 0.25H_2O$: C, 73.09; H, 5.20; N, 3.71. Found: C, 73.19; H, 5.30; N, 3.80.

EXAMPLE 16

N-[9H-(Fluorenyl-9-ethoxycarbonyl)]-4-aminophenyltetrazole

To a solution of 9-fluorenyl ethanol (5.0 g, 23.8 mmol) and 190 mg (2.4 mmol) of pyridine in 50 ml of $CH_2Cl_2$ at 0° C. was added 3.5 g (11.8 mmol) of triphosgene. The mixture was stirred at 0° C. for 1 hour, then at room temperature for 3 hours. To this solution was added 2.8 g (23.78 mmol) of p-aminobenzonitrile in 15 ml of CH₂Cl₂. The mixture was stirred for 20 hours, washed with 10% Na₂CO₃, 10% HCl, dried with MgSO₄, and concentrated to afford a residue which was diluted with 10% ethyl acetate/hexane to obtain N-[9H-(fluorenyl-9-ethoxycarbonyl)]-4-aminobenzonitrile as a white solid, mp 161°–163° C. (6.0 g, 70%).

To a solution containing the above nitrile (5.85 g, 16.36 mmol) in 70 ml of N-methyl-2-pyrrolidinone was added 3.4 g (52.3 mmol) of sodium azide and 3.4 g (24.7 mmol) of triethylamine hydrochloride. The mixture was heated in a sealed tube at 130° C. for 3 hours, cooled, and 200 ml of water was added, acidified to pH=1 with 10% HCl (caution: possibility of hydrazonic acid formation) and extracted with ethyl acetate. The extract dried with MgSO₄, and concentrated to a brown liquid. This was diluted with ethyl acetate and the tetrazole was extracted with 10% NaOH. The basic solution was acidified to pH=2. The white solid was collected and dried. Recrystallization from MeOH provided 4.0 g (62%) of tetrazole was white powder, mp 238°–240° C. IR (KBr): 1702, 1604, 1542, 1511, 1434, 1339, 1244, 1095, 1054, 853, 745 cm⁻¹. ¹NMR (300 MHz, DMSO-d₆) δ 2.32 (q, 2H, J=7.0 Hz), 4.02 (t, 2H, J=7.0 Hz) 4.13 (t, 1H, J=7.0 Hz), 7.31– 7.93 (m, 12H), 9.98 (s, 1H) . Anal. calcd for C₂₃H₁₉N₅O₂: C, 69.51; H, 4.82; N,17.62. Found: C, 69.43; H, 4.87; N, 17.66.

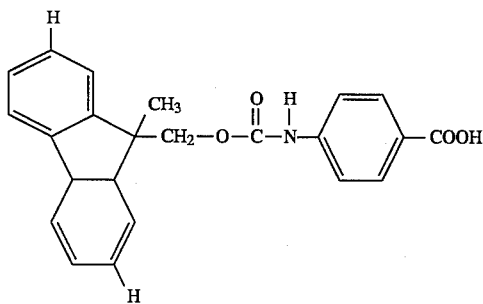

EXAMPLE 17

N-(2-[(9-methyl-9H-fluoren-9-yl]-ethoxycarbonyl-4 -aminobenzoic acid a) 9-Methylfluorene.

To a solution of fluorene (10.0 g, 60.0 mmol) in 100 mL of THF was added n-BuLi (66.6 mmol) at −78° C. This solution was then added to a chilled solution of iodomethane (15.04 g, 90.6 mmol) in 60 mL of THF. The temperature was kept at about −20° C. to maintain a clear solution. The mixture was allowed to warm to room temperature and then quenched with saturated aqueous NH₄Cl and evaporated to a residue which was partitioned between ethyl acetate and water. The organic layer was washed with brine, dried with MgSO₄, filtered and evaporated to a solid. This solid was dissolved with hot pentane, stirred with decolorizing charcoal, filtered through a celite pad, and evaporated to get 10.0 g(92%) of 9-methyl fluorene was a white solid, mp 42°–43° C. FT-IR (KBr): 3065, 3039, 3016, 2962, 2926, 2864, 1478, 1445, 1309, 1023, 792 cm⁻¹. NMR (300 MHz, CHCl₃) δ 1.60–1.62(d, 3H, J=7.5 Hz), 3.93– 3.97 (q, 1H, J=7.5 Hz), 7.32–7.38 (m, 4H) , 7.35– 7.36 (d, 2H, J=8.0 Hz), 7.81–7.83(d, 2H, J=8.0 Hz).

b) 9-Methylfluorene-9-ethanol.

To a solution of 9 -methylfluorene (10.0 g, 55.5 mmol) in 100 mL of THF was added n-BuLi (61.0 mmol) at −10° C., then a solution of ethylene oxide (61.0 mmol) in THF was added in one portion. The reaction mixture was stirred at −20° C., then allowed to warm to room temperature, quenched with NH₄Cl solution and evaporated to a residue. This was then partitioned between ethyl acetate and water, the organic layer was washed with brine, dried with MgSO₄ and evaporated to get the product which was purified by chromatography using 10% ethyl acetate/hexane mixture to provide a pure sample of 9-methylfluorene-9-ethanol, m.p. 84°–85° C.

c) N-{2-[(9-Methyl-9H-fluoren-9-yl]-ethoxycarbonyl-4 -aminobenzoic acid.

To a solution of 9 -methylfluorene-9-ethanol (6.5 g, 28.9 mmol) in 60 mL of THF was added 18.6 Ml (35.9 mmol) of phosgene solution in toluene. Stirred for 3 hours, then excess phosgene was removed by passing argon and by trapping it in KOH solution. The material was evaporated to a residue which was then dissolved in 100 mL THF and added to a solution of p-aminobenzoic acid (7.9 g, (57.8 mmol) in 100 mL of THF. Concentrated to a slurry, then filtered, washed with 1N HCl solution, dried, mp 192°–193° C., FT-IR (KBr): 3467, 3250, 3165, 3039, 2992, 2869, 2666, 2553, 1707, 1679, 1604, 1522, 1458, 1419, 1355, 1311, 1291, 1237, 1216, 1180, 1054, 851, 735 cm⁻¹. NMR (300 MHz, DMSO-d₆); δ 1.87 (br, 1H, 1.48(S, 3H), 32.47 (t, 2H), 3.38 (t, 2H), 7.30–7.91 (m, 8H), 9.84 (s, 1H). Anal. Calcd for C₂₄H₂₁NO₄: C, 74.40; H, 5.46; N, 3.02. Found: C, 74.46; H, 5.48; N, 3.64.

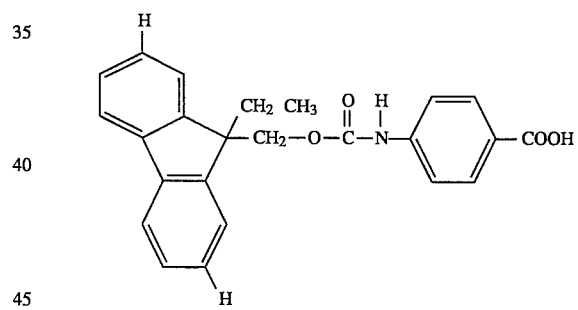

EXAMPLE 18

N-{2-[(9-Ethyl-9H-fluoren-9-yl]-ethoxycarbonyl-4 -aminobenzoic acid

The procedure of Example 17 was repeated to form 9 -ethylfluorene-9-ethanol as the product of steps a and b, giving 5.67 g (92.4%, m.p. 105°–107° C.). N-{2-[9-Ethyl-9H-fluoren-9-yl]-ethoxycarbonyl-4-aminobenzoic acid was prepared according to step c described above. FT-IR (KBr): 3397, 3322, 3065, 3008, 2957, 2931, 2898, 2875, 2669, 2546, 1710, 1676, 1610, 1594, 1440, 1417, 1314, 1288, 1229, 1178, 1067, 754 cm⁻¹. NMR (300 MHz, DMSO-d₆): δ 0.32 (t, 3H), 2.01 (q, 2H), 2.48 (t, 2H), 2.6 (br S, 1H), 3.52 (t, 2H), 7.34 (m, 4H), 7.41 (m, 2H), 7.73 (d, 2H), 7.91 (d, 2H) , 8.63 (br, 1H) . Anal. Calcd for C₂₅H₂₃NO₄: C, 74.80; H, 5.77; N, 3.59. Found: C, 74.71; H, 3.77; N, 3.54.

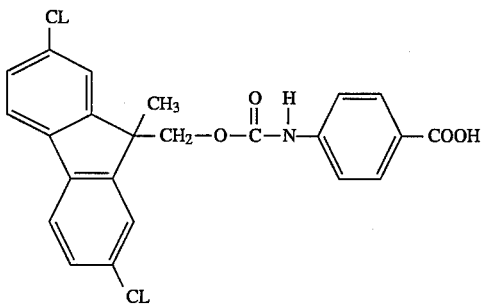

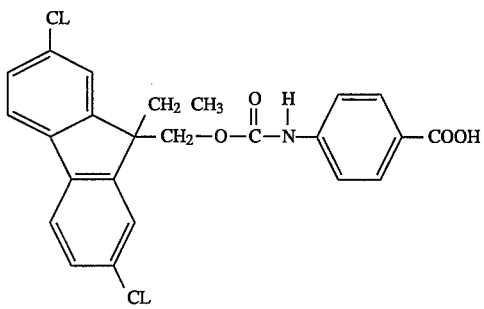

EXAMPLE 19

N-[9-methyl-(2,7-dichlorofluorenyl-9-ethoxycarbonyl)]-4-aminobenzoic acid.

a) 2,7-dichloro-9-methylfluorene.

9-Methylfluorene (43.6 g, 0.24 mol) and N-chlorosuccinimide (64.5 g, 0.48 mol) were suspended in 25 mL of acetonitrile and cooled in an ice-water bath. Then 20 mL of concentrated HCl was added dropwise and the solution was stirred at room temperature overnight. The precipitate was filtered and dried. Recrystallization from EtOH and water gave 24 g (41%) of 2,7-dichloro-9-methylfluorene as white crystals, mp 110°–112° C. FT IR: 3425, 1450, 1407, 1273, 1167, 1070, 851,818 cm$^{-1}$; H$^1$ NMR (CDCl$_3$, 300 MHz) δ 7.3–7.8 (m, 6H, 3.9–4.1 (q, 1H), 1.2–1.3 (d, 2H).

b) 2,7-Dichloro-9-methylfluorene-9-ethanol.

To a solution of 2,7-dichloro-9-methylfluorene (2.1 g, 8.4 mmol) in 20 mL of THF was added 2.5M n-BuLi in hexane (3.36 mL, 8.4 mmol) at −78° C. and stirred for 0.5 hours under argon. To this solution 1.65M ethylene oxide in THF (7.27 mL, 12 mmol) was added rapidly and the solution was allowed to warm to room temperature slowly. Quenched with NH$_4$Cl solution, concentrated to a residue, then extracted with ethyl acetate. The organic layer was dried with MgSO$_4$ and concentrated under reduced pressure to a residue which upon silica gel column chromatographic purification using 20% ethylacetate/hexane provided 1.0 g ( 41% ) of pure product as white solid: H$^1$ NMR (CDCl$_3$, 300 MHz) δ 7.3–8.7 (m, 6H) , 3.0–3.1 (q, 2H), 2.2–2.3 (t, 2H), 1.4–1.5 (s, 3H).

c) N-[9-methyl-(2,7-dichlorofluorenyl-9-ethoxycarbonyl)]-4-aminobenzoic acid.

To a solution of 2,7-dichloro-9-methylfluorene-9-ethanol (2.98 g, 10.16 mmol) in 3 mL of dry THF was added 2 mL (10.36 mmol) of phosgene solution in toluene and stirred at room temperature for 2 hours. It was then concentrated at reduced pressure (properly trapping excess phosgene) and dissolved in 3 mL 1,4-dioxane. This was added to a dioxane/water (1:1) solution containing 4-aminobenzoic acid (1.67 g, 12.19 mmol) and potassium carbonate (1.68 g, 12.19 mmol) and the reaction mixture was stirred overnight. Evaporated off the dioxane, the residue was dissolved in water and acidified to give white solids which was separated and dried, mp 215°– 216° C.: IR 3402, 3312, 1687, 1597, 1538, 1417, 1237, 1175, 1067, 854, 812, 771 cm$^{-1}$; H$^1$ NMR (CDCl$_3$, 300 MHz) δ 12.6–12.8 (s, 1H), 7.4–8.0 (m, 10H), 3.3–3.5 (t, 2H), 2.4–2.6 (t, 2H), 1.4–1.5 (s, 3H) . Anal. Calcd for C$_{24}$H$_{19}$Cl$_2$O$_4$: C, 63.17; H, 4.20; N, 3.07; Cl, 15.54. Found: C, 62.91; H, 4.27; N, 3.00; Cl, 15.44.

EXAMPLE 20

N-[9-ethyl-(2,7-dichlorofluorenyl-9-ethoxy carbonyl)]-4-aminobenzoic acid a) 2,7-Dichloro-9-ethylfluorene.

To a solution of 2,7-dichlorofluorene (1.0 g, 4.3 mmol) in 3 mL of THF was added n-BuLi (2 mL, 5.0 mmol) at −78° C. under argon and the solution was stirred at −78° C. for 0.5 hours. A solution of C$_2$H$_5$I (0.78 g, 5.0 mmol) in 1 mL of THF was poured into the solution and stirred at −78° C. for 15 min, quenched with NH$_4$Cl solution, concentrated and extracted the residue with ethyl acetate, dried with MgSO$_4$ and evaporated to get the crude product which was purified by silica gel column chromatography using hexane as the eluent to obtain 1.35 g (74%) of 2,7-dichloro-9-ethylfluorene was a white solid, mp 80°–83° C.: IR: 3435, 1453, 1422, 1296, 1160, 1072, 885, 807 cm$^{-1}$.H$^1$ NMR (CDCl$_3$, 300 MHz) δ 7.2–7.8 (m, 6H), 3.9–4.1 (t, 1H), 2.0–2.2 (m, 2H), 0.6–0.8 (t, 3H).

b) 2,7-Dichloro-9-ethylfluorene-9-ethanol.

The compound was prepared according to step b of Example 19 to provide: H$^1$ NMR (CDCl$_3$, 300 MHz) d 7.2–7.6 (m, 6H), 2.9–3.1 (m, 2H), 2.2–2.3 (t, 2H), 1.9–2.1 (q, 2H), 0.2–0.3 (t, 3H).

c)

The title compound was obtained according to step c) of Example 19 as a white solid having, mp 212°– 213° C.: IR: 2355, 1702, 1687, 1607, 1527, 1417, 1216, 1175, 1072, 854, 812, 771 cm$^{-1}$.H$^1$ NMR (CDCl$_3$, 300 MHz) d 7.4–8.0 (m, 10H), 3.3–3.4 (t, 2H), 2.4– 2.6 ( t, 2H), 2.1–2.3 (q, 2H), 0.2–0.3 (s, 3H). Anal. Calcd for C$_{25}$H$_{21}$Cl$_2$O$_4$: C, 63.23; H, 4.56; N, 2.94; Cl, 15.07. Found: C, 63.20; H, 4.72; N, 2.93; Cl, 14.92.

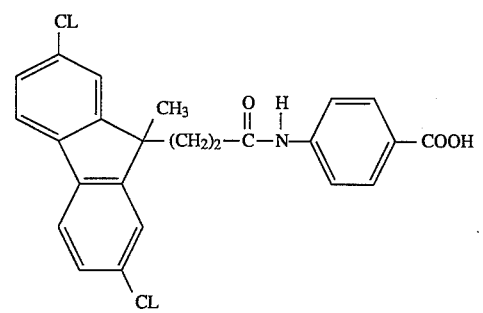

EXAMPLE 21

9-methyl-N-[3-(9-(2,7-dichlorofluorenyl))propionyl]-4-aminobenzoic acid a) and b) 2,7-Dichloro-9-methylfluorenyl-9-propionic acid.

To a solution of 2,7-dichloro-9-methylfluorene (3.23 g, 12.96 mmol) in 20 ml of THF was added n-BuLi (12.96 mmol) at −78° C. After 15 minutes, 2-(2-bromoethyl)-1,3-dioxalane (2.34 g, 12.96 mmol) was added dropwise and the solution was stirred at −78° C. for 2 hours, allowed to warm to room temperature and was further stirred for 2 hours. The mixture was quenched with NH$_4$Cl solution, concentrated to residue, extracted with ethyl acetate. The organic layer was dried with MgSO$_4$ and evaporated to an oil which was subjected to flash silica gel chromatography to give 3.34 g (84%) of 2,7-dichloro-9-methylfluorenylethylacetal. The acetal was dissolved in 15 ml acetone, 24.43 mL (39 mmol) Jones' reagent was added dropwise and stirred at room temperature overnight. The reaction mixture was diluted with water and extracted with ethyl acetate. Silica gel column chromatographic purification using 20% ethyl acetate/hexane gave 1.43 g (34%) of 2,7-dichloro-methylfluorenyl-9-propionic acid as white crystal: H$^1$ NMR (CDCl$_3$, 300 MHz) δ 7.2–7.7 (m, 6H), 2.2–2.4 (m, 2H), 1.5–1.7 (, m2H), 1.4–1.5 (s, 3H).

b) 9-methyl-N-[3-(9-(2,7-dichlorofluorenyl)) propionyl]-4-aminobenzoic acid.

(2,7-Dichlorofluorenyl)-9-propionic acid (1.40 g, 4.36 mmol), ethyl 4-aminobenzoate (0.72 g, 4.36 mmol), (1-(3-dimethylaminopropyl)3-ethyl)carbodiimide hydrochloride (0.90 g, 4.36 mmol) and N-dimethyl aminopyridine (catalytic amount) was suspended in 20 mL of anhydrous methylene chloride under argon and stirred for 18 hours. The solvent was evaporated and the residue after silica gel column separation using 20% ethyl acetate/hexane as eluent gave 1.86 g (91%) of ester as a white solid. The ester was dissolved in 20 mL of MeOH:H$_2$O (6:1), mixed with potassium bicarbonate (2.74 g, 20 mol) and refluxed for 6 hours. The methanol was evaporated and acidified with dilute. HCl to get the product as white solid. It was then recrystallized from aqueous methanol to provide 930 mg (53%) of 9-methyl-N-[3-(9-(2,7-dichlorofluorenyl))propionyl]-4-aminobenzoic acid as a white solid, mp 237° C.–238° C., IR: 3311, 1673, 1602, 1540, 1453, 1409, 1252, 1178, 859, 812, 771. H$^1$ NMR (CDCl$_3$, 300 MHz) d 7.4–8.0 (m, 10H), 2.4–2.5 (t, 2H), 1.5–1.6 (t, 2H), 1.4–1.5 (s, 3H). Anal. Calcd for C$_{24}$H$_{19}$Cl$_2$NO$_3$: C, 65.47; H, 4.34; N, 3.18; Cl, 16.10. Found: C, 65.52; H, 4.34; N, 3.19; C$_{1,\ 16.01}$.

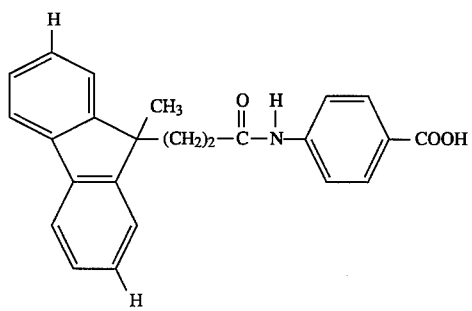

EXAMPLE 22

9-Methyl-N-[3-(9-fluorenyl))propionyl]-4-aminobenzoic acid 3-(9-Fluorenyl)propionic acid. The compound was prepared according to the procedure of Example 21, steps a) and b) and showed H$^1$ NMR (CDCl$_3$, 300 MHz) δ 7.4–8.0 (m, 8H), 2.3–2.4(m, 2H), 1.5–1.6(m, 2H), 1.4–1.5 (s, 3H).

9-Methyl-N-[3-(9-fluorenyl))propionyl]-4-aminobenzoic acid. The compound was prepared by the procedure described in step c of Example 21 and produced a white solid having mp 216° C.–217° C. IR: 3404; 1687; 1597; 1532; 1409; 1311; 1280; 1255; 1175; 859; 764; 735. H$^1$ NMR (CDCl$_3$, 300 MHz) δ 7.4– 8.0(m, 12H), 1.40–1.50(s, 3H) , 2.20–2.40(t, 2H) , 1.40– 1.60(t, 2H). Anal. Calcd for C$_{24}$H$_{21}$NO$_3$: c, 77.61; H, 5.70;,N, 3.77. Found: C, 77.61; H, 5.70; N, 3.74.

EXAMPLE 23

Adjuvant Arthritis

Male Sprague Dawley rats, 150–200 g, were anesthetized with isoflurane. The drug from Example 7, namely N-[9H-(fluorenyl- 9-ethoxycarbonyl)]amino-4-benzoic acid was administered intraperitoneally in 0.5% methylcellulose or water at three doses, 10 mg/kg, 30 mg/kg, 100 mg/kg. The rat was then injected intradermally in the distal third of the tail with 0.1 ml of saline or 0.1 ml of well-sonicated squalene containing 1 mg/ml Mycobacterium tuberculosis. Rats were then returned to their cages. On days 1 and 2 after the adjuvant injection, each rat was weighed and dosed with vehicle or drug suspension as before, but without anesthesia. On day 3, each rat was weighed and anesthetized with sodium pentobarbital. Blood was drawn by cardiac puncture into 0.2 ml of EDTA solution (12 mg/ml). Blood samples were centrifuged and the plasma was removed. The fibrinogen was converted into fibrin using sodium sulfite and the resulting fibrin was assayed using a Lowry protein assay to estimate initial fibrinogen levels. Percent inhibition by test compound was determined by subtracting fibrinogen level in non-Freund's adjuvant-injected rats from fibrinogen levels in rats injected with adjuvant alone and those rats injected with adjuvant plus test compound, and dividing the resultant fibrinogen increases in drug treated animals by fibrinogen levels in rats injected with adjuvant alone minus the levels of non-drug treated animals and multiplying by 100.

The results indicated that plasma fibrinogen concentrations were dose-dependently inhibited to a maximum of 50%, achieved at a dose of 3 mg/kg when the drug was given orally. Basal plasma fibrinogen levels were elevated from 2.44±0.08 mg/ml to 8.6±0.2 mg/ml (n=25), in different experiments. The drug by itself elevated plasma fibrinogen levels to 4.8±0.6 at 100 mg/kg (p.o.)(n=5).

When the test was repeated with the compound of Example 14, namely N-[3-(9-Fluorenyl)propionyl]-anthranilic acid at doses of 10, 30 and 100 mg/kg plasma fibrinogen levels were inhibited 22% 19% and 51% respectively.

EXAMPLE 24

The adjuvant arthritis test of Example 23 was repeated at doses ranging from 0.3 to 100 mg/kg administered intraperitoneally and orally with compounds produced in Examples 7, 8 and 9. The results are set forth in Table 1.

TABLE I

| Example | AA* (i.p.) % inhibition at (100 mg/kg) | AA* (p.o.) Dose yielding max inhibition (100 mg/kg) |
|---|---|---|
| 7 | 63% | 30 mg/kg |
| 8 | 69% | 100 mg/kg |
| 9 | 78% | 3 mg/kg |

TABLE I-continued

| Example | AA* (i.p.) % inhibition at (100 mg/kg) | AA* (p.o.) Dose yielding max inhibition (100 mg/kg) |
|---|---|---|

*Inhibited plasma fibrinogen in arthritis model.

EXAMPLE 25

Reverse Passive Arthus Reaction (RPA)

Male SD rats weighing between 200 and 300 g were used. Test compounds were dissolved in dimethyl sulfoxide and 1 ml/kg of this stock solution (100 mg/ml), on serial dilutions were injected intraperitoneally one hour before administration of the antigen or given orally. The animals were anesthetized inhalationally with isoflurane and then injected through the penile vein with 1 ml of a solution of 2.5 mg of Evan's blue dye and 5.0 mg of human serum albumin in 1 ml of saline. This treatment was followed immediately by intracutaneous injections of 0.075 ml of anti-human albumin diluted to contain 4.38 mg/ml of antibody at 2 sites opposite the midline back. Anesthesia was terminated and after three hours, the animals were sacrificed. The skin was removed and the blue stained areas cut out. The skin patches were soaked overnight in stoppered tubes containing 2 ml of 1N potassium hydroxide at 5° C. Then 9 ml of a mixture of five parts of a 1.2N phosphoric acid and thirteen parts of acetone were added to the tubes. The tube contents were agitated and centrifuged, and the absorbance measured at 620 nm. The data were calculated as inhibition of blueing by test compound compared to control animals receiving only antigen and antibody. The RPA inhibition results are reported in Table II.

TABLE II

| Example | RPA (i.p.) $ED_{50}$ | RPA (p.o.) Inhibition at (100 mg/kg) |
|---|---|---|
| 7 | 70 mg/kg | 25% |
| 8 | 100 mg/kg | 0% |
| 9 | 34 mg/kg | 54% |

EXAMPLE 26

Inhibition of Ear Edema Caused by Oxazolone

CF-1 mice, 25–30 g body weight, six animals per group were used. The mice were sensitized to the irritant two weeks prior to the test by dribbling 100 μL of a 3% solution of oxazolone in acetone onto the scrotum of the animal. Test compounds were administered orally at doses of 100 mg/kg and 300 mg/kg for 1 hour prior to oxazolone, intraperitoneally as follows: The test compound was dissolved in dimethyl sulfoxide and doses of 10 mg/kg, 30 mg/kg and 100 mg/kg were injected 15 minutes prior to irritant. The irritant, 3% oxazolone in acetone, was added to the surface of the ear, 5 μl added to the upper surface and 5 μl added to the lower surface. After twenty four hours, the thickness of the ear was measured to 0.01 mm by a micrometer with loose drag, positioned at the lateral-most edge of the midpoint of the pinna. Data were calculated as the inhibition of increased ear thickness compared to control animals' receiving only the irritant. In general, % inhibition of greater than 20% is statistically significant (p<0.05 or less, Student's t-test for unpaired data).

The results indicated that oxazolone increased ear thickness from a value of 0.3 mm to 0.6 mm. The drug from Example 7 inhibited this response in a dose-dependent manner by 46%, 82% and 79%, at doses of 10, 30 and 100 mg/kg, respectively, when given i.p., and by 50% when given orally.

EXAMPLE 27

Determination of Myeloperoxidase (MPO) Activity

Colonic tissues were assessed biochemically by the activity of the neutrophil marker enzyme, MPO. Approximately 50 mg of mucosal scrapings were homogenized (30 sec, 4° C.) in 1 ml of 0.5% hexadecyltrimethylammonium bromide detergent. The homogenate was then sonicated (10 sec), subjected to three freeze thaw cycles, and centrifuged (15 min, 40,000 g). MPO was assayed spectrophotometrically by determining the decomposition of peroxide using o-dianisidine as the hydrogen donor. Data was expressed as the mean absorbance (460 nm)±S.E.M. at 15 min, per gram wet weight.

The drug of Examples 7 and 9 were tested orally for their ability to inhibit acetic acid induced colonic inflammation as measured by myeloperoxidose activity (MPO) and/or by dye extravasation, at doses ranging from 1 mg/kg to 100 mg/kg. Acetic acid caused a 25-fold increase in MPO activity.

The invention being thus described, it will be obvious that the same may be varied in many ways. Such variations are not to be regarded as a departure from the spirit and scope of the invention and all such modifications are intended to be included within the scope of the following claims.

What is claimed:

1. A compound having the formula:

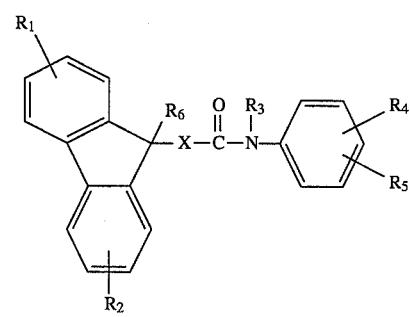

wherein:

X is selected from the group consisting of methylene, oxygen, ethylene, methyleneoxy, and ethyleneoxy;

$R_1$ and $R_2$ are independently selected from the group consisting of hydrogen, $C_1$ to $C_6$ lower alkyl, aryl, aralkyl, alkoxy, alkoxyalkyl, halogen and nitro;

$R_3$ is selected from the group consisting of hydrogen and $C_1$ to $C_6$ lower alkyl groups;

$R_4$ is selected from the group consisting of -$CO_2H$; -$NHSO_2R_7$, wherein $R_7$ is methyl, or trifluoromethyl; -$CONHSO_2R_8$, wherein $R_8$ is methyl, trifluoromethyl, or phenyl; 1H-tetrazol-5-yl; and -CONH-tetrazol-5-yl;

$R_5$ is selected from the group consisting of hydrogen, $C_1$ to $C_6$ lower alkyl, halogen, hydroxyl, and a methoxy group; and $R_6$ is selected from the group consisting of hydrogen, halogen, $C_1$ to $C_6$ lower alkyl, $C_1$ to $C_6$ lower alkoxy, $C_1$ to $C_6$ lower alkoxy ethers, and alicyclic hydrocarbo groups.

2. The compound of claim 1, wherein $R_1$, $R_2$ and $R_3$ are independent selected from the group consisting of hydrogen, chlorine and mixtures thereof.

3. The compound of claim 1, wherein $R_1$ and $R_2$ are selected from the group consisting of 2,7-dimethyl, 2,7-diethyl, 2,7-di-t-butyl, and 2,7-dichloro.

4. The compound of claim 1, wherein $R_4$ is selected from the group consisting of -2-$CO_2H$, -3-$CO_2H$, -4-$CO_4H$, and -4-$CH_2CO_2H$.

5. The compound of claim 1, wherein $R_5$ is selected from the group consisting of hydrogen, hydroxyl, and methyl group.

6. The compound of claim 5, wherein $R_5$ is -2-hydroxyl.

7. The compound of claim 1, wherein $R_1$ and $R_3$ are independently selected from the group consisting of hydrogen and chlorine, and wherein $R_6$ is selected from the group consisting of methyl and ethyl.

8. The compound of claim 1, selected from the group consisting of:

N-[9H-(fluorenyl-9-ethoxycarbonyl)]amino-4-benzoic acid,

N-[9H-(2,7-dimethylfluorenyl-9-ethoxycarbonyl)] amino-4 -benzoic acid,

N-[9H-(2,7-dichlorofluorenyl-9-ethoxycarbonyl)] amino-4 -benzoic acid,

N-[9H-(2,7-di-t-butylfluorenyl-9-ethoxycarbonyl)] amino-4-benzoic acid,

N-[9H-(2,7-diethylfluorenyl-9-ethoxycarbonyl)]amino-4-benzoic acid,

N-[9H-(fluorenyl-9-ethoxycarbonyl)]-4-aminophenyltetrazole,

N-[9H-(fluorenyl-9-ethoxycarbonyl)]amino-3-benzoic acid,

N-[9H-(fluorenyl-9-ethoxycarbonyl)]anthranilic acid,

N-[3-(9-fluorenyl)proprionyl]anthranilic acid,

N-[9H-(fluorenyl-9-methoxycarbonyl)]-N-methylanthranilic acid,

N-[9H-(fluorenyl-9-ethoxycarbonyl)]-4-aminosalicylic acid,

N-[3-(9-fluorenyl)propionyl]-4-aminosalicylic acid,

N-[9H-(fluorenyl-9-methoxycarbonyl)]-4-aminophenylacetic acid,

N-[9H-(fluorenyl-9-ethoxycarbonyl)]-4-aminophenylacetic acid,

N-[9H-(fluorenyl-9-methoxycarbonyl)]-4-aminophenyl-α-methylacetic acid,

N-(fluorenyl-9-methoxycarbonyl)-$N^1$-acetylsulfanilamide,

N-{2-[9-methyl-9H-fluoren-9-yl]-ethoxycarbonyl-4-aminobenzoic acid,

N-{2-[9-ethyl-9H-fluoren-9-yl]-ethoxycarbonyl-4-aminobenzoic acid,

N-[9-methyl-(2,7-dichlorofluorenyl-9-ethoxycarbonyl)]-4-aminobenzoic acid,

N-[9-ethyl-(2,7-dichlorofluorenyl-9-ethoxy carbonyl)]-4-aminobenzoic acid, 9-methyl-N-[3-(9-(2,7-dichlorofluorenyl))propionyl]-4-aminobenzoic acid, 9-methyl-N-[3-(9-fluorenyl))propionyl]-4-aminobenzoic acid, N-(9H-fluorenyl-9-oxycarbonyl)-4-aminobenzoic acid, and N-{[9H-(fluorenyl-9-ethoxycarbonyl)]-4-amino-benzoyl}-benzenesulfonamide.

9. A method of treating an inflammatory condition comprising administering to an animal in need of such treatment an amount of at least one compound represented by the following formula:

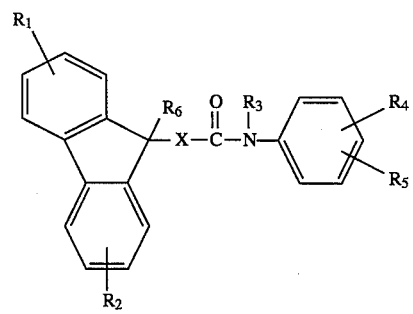

wherein:

X is selected from the group consisting of methylene, oxygen, ethylene, methyleneoxy, and ethyleneoxy;

$R_1$ and $R_2$ are independently selected from the group consisting of hydrogen, $C_1$ to $C_6$ lower alkyl, aryl, aralkyl, alkoxy, alkoxyalkyl, halogen, and nitro;

$R_3$ is selected from the group consisting of hydrogen and $C_1$ to $C_6$ lower alkyl groups;

$R_4$ is selected from the group consisting of -$CO_2H$; -$NHSO_2R_7$, wherein R7 is methyl, or trifluoromethyl; -$CONHSO_2R_8$, wherein $R_8$ is methyl, trifluoromethyl, or phenyl; 1H-tetrazol-5-yl; and -CONH-tetrazol-5-yl;

$R_5$ is selected from the group consisting of hydrogen, $C_1$ to $C_6$ lower alkyl, halogen, hydroxyl, and a methoxy group; and $R_6$ is selected from the group consisting of hydrogen, halogen, $C_1$ to $C_6$ lower alkyl, $C_1$ to $C_6$ lower alkoxy, $C_1$ to $C_6$ lower alkoxy ethers, and alicyclic hydrocarbon groups.

10. The method of claim 9, wherein $R_1$, $R_2$ and $R_3$ are independently selected from the group consisting of hydrogen, chlorine and mixtures thereof.

11. The method of claim 9, wherein $R_1$ and $R_2$ are selected from the group consisting of 2,7-dimethyl, 2,7-diethyl, 2,7-di-t-butyl, and 2,7-dichloro.

12. The method of claim 9, wherein $R_4$ is selected from the group consisting of -2-$CO_2H$, -3-$CO_2H$, -4-$CO_2H$, and -4-$CH_2CO_2H$.

13. The method of claim 9, wherein $R_5$ is selected from the group consisting of hydrogen, hydroxyl, and methyl groups.

14. The method of claim 13, wherein $R_5$ is -2-hydroxyl.

15. The compounds of claim 9, where $R_1$ and $R_2$ are independently selected from the group consisting of hydrogen, chlorine and mixtures thereof, and wherein $R_6$ is selected from the group consisting of methyl and ethyl.

16. The method of claim 9, selected from the group consisting of:

N-[9H-(fluorenyl-9-ethoxycarbonyl)]amino-4-benzoic acid,

N-[9H-(2,7-dimethylfluorenyl-9-ethoxycarbonyl)]amino-4-benzoic acid,

N-[9H-(2,7-dichlorofluorenyl-9-ethoxycarbonyl)]amino-4-benzoic acid,

N-[9H-(2,7-di-t-butylfluorenyl-9-ethoxycarbonyl)]amino-4-benzoic acid,

N-[9H-(2,7-diethylfluorenyl-9-ethoxycarbonyl)]amino-4-benzoic acid,

N-[9H-(fluorenyl-9-ethoxycarbonyl)]-4-aminophenyltetrazole,

N-[9H-(fluorenyl-9-ethoxycarbonyl)]amino-3-benzoic acid,

N-[9H-(fluorenyl-9-ethoxycarbonyl)]anthranilic acid,

N-[3-(9-fluorenyl)proprionyl]anthranilic acid,

N-[9H-(fluorenyl-9-methoxycarbonyl)]-N-methylanthranilic acid,

N-[9H-(fluorenyl-9-ethoxycarbonyl)]-4-aminosalicylic acid,

N-[3-(9-fluorenyl)propionyl]-4-aminosalicylic acid,

N-[9H-(fluorenyl-9-methoxycarbonyl)]-4-aminophenylacetic acid,

N-[9H-(fluorenyl-9-ethoxycarbonyl)]-4-aminophenylacetic acid,

N-[9H-(fluorenyl-9-methoxycarbonyl)]-4-aminophenyl-α-methylacetic acid,

N-(fluorenyl-9-methoxycarbonyl)-$N^1$-acetylsulfanilamide,

N-{2-[9-methyl-9H-fluoren-9-yl]-ethoxycarbonyl-4-aminobenzoic acid,

N-{2-[9-ethyl-9H-fluoren-9-yl]-ethoxycarbonyl-4-aminobenzoic acid,

N-[9-methyl-(2,7-dichlorofluorenyl-9-ethoxycarbonyl)]-4-aminobenzoic acid,

N-[9-ethyl-(2,7-dichlorofluorenyl-9-ethoxy carbonyl)]-4-aminobenzoic acid, 9-methyl-N-[3-(9-(2,7-dichlorofluorenyl))propionyl]-4-aminobenzoic acid, 9-methyl-N-[3-(9-fluorenyl))propionyl]-4-aminobenzoic acid, N-(9H-fluorenyl-9-oxycarbonyl)-4-aminobenzoic acid, and N-{[9H-(fluorenyl-9-ethoxycarbonyl)]-4-amino-benzoyl}-benzenesulfonamide.

17. A pharmaceutical composition suitable for use in producing an anti-inflammatory effect in an animal comprising, as an active ingredient, an amount of at least one compound of the following formula administered to an animal together with a pharmaceutically acceptable carrier or diluent

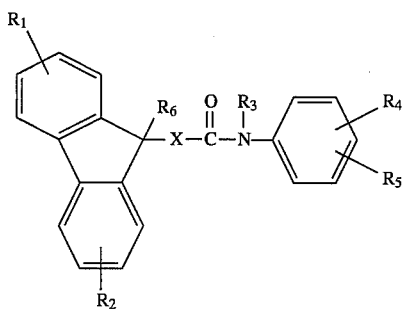

wherein:

X is selected from the group consisting of methylene, oxygen, ethylene, methyleneoxy, and ethyleneoxy;

$R_1$ and $R_2$ are independently selected from the group consisting of hydrogen, $C_1$ to $C_6$ lower alkyl, aryl, aralkyl, alkoxy, alkoxyalkyl, halogen, and nitro;

$R_3$ is selected from the group consisting of hydrogen, and $C_1$ to $C_6$ lower alkyl groups;

$R_4$ is selected from the group consisting of $-CO_2H$; $-NHSO_2R_7$, wherein $R_7$ is methyl, or trifluoromethyl; $-CONHSO_2R_8$, wherein $R_8$ is methyl, trifluoromethyl, or phenyl; 1H-tetrazol-5-yl; and -CONH-tetrazol-5-yl;

$R_5$ is selected from the group consisting of hydrogen, $C_1$ to $C_6$ lower alkyl, halogen, hydroxyl, and a methoxy group; and $R_6$ is selected from the group consisting of hydrogen, halogen, $C_1$ to $C_6$ lower alkyl, $C_1$ to $C_6$ lower alkoxy, $C_1$ to $C_6$ lower alkoxy ethers, and alicyclic hydrocarbo groups.

18. The pharmaceutical composition of claim 17, wherein $R_1$, $R_2$, and $R_3$ are independently selected from the group consisting of hydrogen, chlorine and mixtures thereof.

19. The pharmaceutical composition of claim 17, wherein $R_1$ and $R_2$ are selected from the group consisting of 2,7-dimethyl, 2,7-diethyl 2,7-di-t-butyl, and 2,7-dichloro.

20. The pharmaceutical composition of claim 17, wherein $R_4$ is selected from the group consisting of $-2-CO_2H$, $-3-CO_2H$, and $4-CH_2CO_2H$.

21. The pharmaceutical composition of claim 17, wherein $R_5$ is selected from the group consisting of hydrogen, hydroxyl, and methyl groups.

22. The pharmaceutical composition of claim 21, wherein $R_5$ is -2-hydroxyl.

23. The compound of claim 17 wherein $R_1$ and $R_2$ are independently selected from the group consisting of hydrogen, chlorine and mixtures thereof, and wherein $R_6$ is selected from the group consisting of methyl, ethyl and mixtures thereof.

24. The pharmaceutical composition of claim 17, selected from the group consisting of:

N-[9H-(fluorenyl-9-ethoxycarbonyl)]amino-4-benzoic acid,

N-[9H-(2,7-dimethylfluorenyl-9-ethoxycarbonyl)]amino-4-benzoic acid,

N-[9H-(2,7-dichlorofluorenyl-9-ethoxycarbonyl)]amino-4-benzoic acid,

N-[9H-(2,7-di-t-butylfluorenyl-9-ethoxycarbonyl)]amino-4-benzoic acid,

N-[9H-(2,7-diethylfluorenyl-9-ethoxycarbonyl)]amino-4-benzoic acid,

N-[9H-(fluorenyl-9-ethoxycarbonyl)]-4-aminophenyltetrazole,

N-[9H-(fluorenyl-9-ethoxycarbonyl)]amino-3-benzoic acid,

N-[9H-(fluorenyl-9-ethoxycarbonyl)]anthranilic acid,

N-[3-(9-fluorenyl)proprionyl]anthranilic acid,

N-[9H-(fluorenyl-9-methoxycarbonyl)]-N-methylanthranilic acid,

N-[9H-(fluorenyl-9-ethoxycarbonyl)]-4-aminosalicylic acid,

N-[3-(9-fluorenyl)propionyl]-4-aminosalicylic acid,

N-[9H-(fluorenyl-9-methoxycarbonyl)]-4-aminophenylacetic acid,

N-[9H-(fluorenyl-9-ethoxycarbonyl)]-4-aminophenylacetic acid,

N-[9H-(fluorenyl-9-methoxycarbonyl)]-4-aminophenyl-α-methylacetic acid,

N-(fluorenyl-9-methoxycarbonyl)-N$^1$-acetylsulfanilamide,

N-{2-[9-methyl-9H-fluoren-9-yl]-ethoxycarbonyl-4-aminobenzoic acid,

N-{2-[(9-ethyl-9H-fluoren-9-yl]-ethoxycarbonyl-4-aminobenzoic acid,

N-[9-methyl-(2,7-dichlorofluorenyl-9-ethoxycarbonyl)]-4-aminobenzoic acid,

N-[9-ethyl-(2,7-dichlorofluorenyl-9-ethoxy carbonyl)]-4-aminobenzoic acid, 9-methyl-N-[3-(9-(2,7-dichlorofluorenyl))propionyl]-4-aminobenzoic acid, 9-methyl-N-[3-(9-fluorenyl))propionyl]-4-aminobenzoic acid, N-(9H-fluorenyl-9-oxycarbonyl)-4-aminobenzoic acid, and N-{[9H-(fluorenyl-9-ethoxycarbonyl)]-4-amino-benzoyl}-benzenesulfonamide.

25. The pharmaceutical composition of claim 17 which is administered orally.

26. The pharmaceutical composition of claim 17 which is administered, parenterally, rectally or topically.

27. The pharmaceutical composition of claim 17 in the form of a powder, lotion, gel, ointment, cream, or sterile aqueous solution.

28. The pharmaceutical composition of claim 17 which is administered transdermally.

* * * * *

UNITED STATES PATENT AND TRADEMARK OFFICE
CERTIFICATE OF CORRECTION

PATENT NO. : 5,472,973

DATED : December 5, 1995

INVENTOR(S) : John J. Perumattam

It is certified that error appears in the above-indentified patent and that said Letters Patent is hereby corrected as shown below:

Claim 8, column 25, line 27, change "amino-4 -benzoic" to —amino-4-benzoic—;

Claim 8, column 25, line 29, change "amino-4 -benzoic" to —amino-4-benzoic—;

Claim 8, column 26, line 2, change "aminobenzoic acid" to —aminobenzoic acid—;

Claim 12, column 26, line 52, change "4-$CH_2CO_2H$" to —4-$CH_2CO_2H$—;

Claim 16, column 27, line 28, change "4ami" to —4-ami—;

Claim 16, column 27, line 41, change "aminobenzoic acid," to —aminobenzoic acid,—; and

UNITED STATES PATENT AND TRADEMARK OFFICE
CERTIFICATE OF CORRECTION

PATENT NO. : 5,472,973
DATED : December 5, 1995
INVENTOR(S) : John J. Perumattam It is certified that error appears in the above-indentified patent and that said Letters Patent is hereby corrected as shown below:

Claim 24, column 30, line 1, change "aminobenzoic acid" to --aminobenzoic acid--.

Signed and Sealed this

Ninth Day of April, 1996

*Attest:*

BRUCE LEHMAN

*Attesting Officer*     Commissioner of Patents and Trademarks